United States Patent
Wagner

(10) Patent No.: US 7,678,736 B1
(45) Date of Patent: Mar. 16, 2010

(54) MODIFIED REACTIVE SORBENTS EXHIBITING ENHANCED DECONTAMINATION OF CHEMICAL WARFARE AGENTS

(75) Inventor: George W. Wagner, Elkton, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 646 days.

(21) Appl. No.: 11/467,964

(22) Filed: Aug. 29, 2006

(51) Int. Cl.
*B01J 20/22* (2006.01)

(52) U.S. Cl. .................. 502/401; 502/526

(58) Field of Classification Search .......... 502/401, 502/402, 526
See application file for complete search history.

(56) References Cited

U.S. PATENT DOCUMENTS

| | | | | |
|---|---|---|---|---|
| 4,576,927 | A | * | 3/1986 | Kuroda et al. .......... 502/402 |
| 6,537,382 | B1 | * | 3/2003 | Bartram et al. .......... 134/7 |

* cited by examiner

*Primary Examiner*—Edward M Johnson
(74) *Attorney, Agent, or Firm*—Ulysses John Biffoni; Herbert C. Rose

(57) ABSTRACT

A composition for decontaminating a highly toxic material, wherein the composition includes a modified reactive sorbent comprising a reactive sorbent in combination with a sufficient amount of an organic solvent to saturate the pores of the reactive sorbent to yield a non-slurry, free flowing mixture. The present invention is further directed to a method for making such compositions and method for decontaminating surfaces using such compositions.

31 Claims, No Drawings

MODIFIED REACTIVE SORBENTS EXHIBITING ENHANCED DECONTAMINATION OF CHEMICAL WARFARE AGENTS

GOVERNMENT INTEREST

The invention described herein may be manufactured, used and licensed by or for the U.S. Government.

FIELD OF THE INVENTION

The present invention relates to compositions useful for decontamination of surfaces contaminated with highly toxic materials, including chemical warfare agents and/or industrial chemicals, insecticides and the like, and more particularly to modified reactive sorbents exhibiting enhanced decontamination of such highly toxic materials.

BACKGROUND OF THE INVENTION

Exposure to highly toxic materials, and especially chemical warfare agents, is a potential hazard to both the armed forces and civilian populations. Such chemical warfare agents possess toxic properties capable of killing, injuring or incapacitating people. It has been estimated that about 25 to 27 nations currently possess chemical weapons, often referred to as the "poor man's nuclear weapon." The manufacture of chemical warfare agents in small quantities by terrorists is an ongoing threat, and the manufacture and use of military quantities of chemical warfare agents for delivery against U.S. troops is always a real potential.

Some commonly known chemical warfare agents are bis-(2-chloroethyl) sulfide (HD or mustard gas), pinacolyl methylphosphonofluoridate (GD) and O-ethyl S-(2-diisopropylamino)ethyl methylphosphonothioate (VX), as well as analogs and derivatives of these agents. These chemical warfare agents are generally delivered as fine aerosol mists which, aside from presenting an inhalation threat, will deposit on surfaces of military equipment and hardware, including uniforms, weapons, vehicles, vans and shelters. Once such equipment and hardware is contaminated with one of the previously mentioned highly toxic materials, the agent must be removed in order to minimize contact hazards.

For this reason, there is a crucial need to develop and improve technology for decontamination of highly toxic materials. This is especially true for the class of toxic agents known as nerve agents or nerve gases which are produced and stockpiled for both industrial use and as chemical warfare agents. Simply by way of example, one class of nerve agents with a high level of potential lethality is the class that includes organophosphorus-based ("OP") compounds, such as Sarin, Soman, and VX. Such agents can be absorbed through inhalation and/or through the skin of an animal or person. The organophosphorus-type ("OP") CW materials typically manifest their lethal effects against animals and people by inhibiting acetylcholine esterase ("AChE") enzyme at neuromuscular junctions between nerve endings and muscle tissue to produce an excessive buildup of the neurotransmitter acetylcholine, in an animal or person. This can result in paralysis and death in a short time.

In addition to the concerns about chemical warfare agents, there is also a growing need in industry for decontamination of industrial chemicals and/or insecticides, for example, ACHE-inhibiting pesticides such as parathion, paraoxon and malathion, among others. Thus, it is very important to be able to effectively detoxify a broad spectrum of toxic agents, including, but not limited to, organophosphorus-type compounds, from contaminated surfaces and sensitive equipment.

Chemical warfare agents and related toxins are so hazardous that simulants have been developed for purposes of screening decontamination and control methods.

These simulants are 2-chloroethylphenyl sulfide (CEPS), an HD simulant, dimethyl methyl phosphonate (DMMP), a G-agent simulant, and O,S-diethylphenylphosphonothioate (DPPT), a VX simulant.

The U.S. Army uses a decontamination material called XE555 resin (Ambergard™ Rohm & Haas Company, Philadelphia, Pa.). XE555 is presently being used by the military for immediate decontamination applications. The objective of immediate decontamination operations is to remove toxic agents from the contaminated surface as rapidly as possible. However, XE555 has several disadvantages. Although effective at removing chemical agents, XE555 does not possesses sufficient reactive properties to neutralize the toxic agent(s) picked up by this resin. Thus, after use for decontamination purposes, XE555 itself presents an ongoing threat from off-gassing toxins and/or vapors mixed with the resin. In addition, XE555 is relatively expensive in the quantities required for decontamination purposes.

Recently, reactive sorbents have been developed and used to both absorb and react with highly toxic materials to yield less toxic products. For example, the U.S. Army uses M100 sorbent decontamination system (SDS) for decontamination of highly toxic materials. The M100 SDS utilizes an alumina-based reactive sorbent called A-200-SiC-1005S, which is in the form of a powder. The reactive sorbent powder acts as an inexpensive, non-corrosive, non-harmful absorber designed to be rubbed onto a contaminated surface and does not require water rinse or special disposal. The reactive sorbent is structured to flow readily across a contaminated surface, and is highly porous, allowing it to absorb the highly toxic material quickly. The absorbed highly toxic material is strongly retained within the pores of the sorbent, which reacts to form less toxic products, thereby minimizing off-gassing and contact hazards.

Bartram and Wagner (U.S. Pat. No. 5,689,038, incorporated by reference herein) report the use of an aluminum oxide and a mixture of aluminum oxide and magnesium monoperoxyphthalate (MMPP) as reactive sorbents to decontaminate surfaces contacted with droplets of chemical warfare agents. It has been reported that both materials were able to effectively remove such toxic agents from a surface to the same extent as XE555. In addition, both materials represented improvements in chemical warfare agent degrading reactivity and in reducing off-gassing of toxins relative to XE555. The reported sorbents were based on pre-existing, commercially available materials, such as Selexsorb CD™, a product of the Alcoa Company. Essentially, Bartram and Wagner reported that their aluminum oxide is modified by size reduction, grinding or milling.

Bartram and Wagner (U.S. Pat. No. 6,537,382, incorporated by reference herein) report the use of two types of reactive sorbents. One comprises metal exchanged zeolites such as silver-exchanged zeolite, and the other comprises sodium zeolites. The reactive sorbents are disclosed to remove chemical agents from the surface being decontaminated, and then begin decomposing the absorbed chemical agents. Similar in all reactive sorbents, this dual action provides the advantage of reducing the risks associated with potential outgassing from the sorbent, and reducing the toxicity of the sorbent for disposal purposes.

Although, current forms of reactive sorbents as solid—phase decontaminants are capable of absorbing and removing highly toxic materials including chemical warfare agents from surfaces, their capacity to react with the highly toxic materials is limited and prolonged as compared to liquid-phase decontaminants. Thus, for a time after application, the contaminated reactive sorbents present a persistent hazard as the highly toxic materials slowly react and decompose in the sorbents.

Applicant has theorized that the primary reason why reactive sorbents react slowly with highly toxic materials including chemical warfare agents is the slow diffusion of the materials once they are absorbed. The absorbed materials in the form of droplets are concentrated within the pores of the reactive sorbent, and depending on volatility, typically spread across the surface at a slow rate. It is therefore believed that the slow diffusion of the highly toxic materials within the reactive sorbent results in low reactivity. To enhance diffusion, solvents may be employed to spread and more uniformly distribute the highly toxic materials across the surface of the reactive sorbent. This results in a slurry mixture that exhibits enhanced reaction rates relative to the dry powder reactive sorbent. However, the production and handling of a slurry mixture on-site greatly complicates the decontamination process and hinders clean up afterward.

Thus, there remains a need in the art for even more effective, chemically modified forms of reactive sorbents, and for still further compositions and methods, optimized to allow for the rapid and effective removal and/or decontamination of chemical warfare agents and related highly toxic materials in an environmentally acceptable and cost-effective process.

SUMMARY OF THE INVENTION

The present invention relates generally to novel compositions suitable for use as reactive sorbents and methods for preparing and using these novel reactive sorbents in the form of modified reactive sorbents to decontaminate a wide range of highly toxic materials including chemical warfare agents and/or industrial chemicals, insecticides and the like. In order to solve these and other problems in the art, the present invention provides specifically a modified reactive sorbent exhibiting improved reactivity with a highly toxic material for enhancing decontamination of such highly toxic materials in a rapid and efficient manner. The modified reactive sorbents of the present invention further exhibits enhanced resistance to deactivation of its surface reactivity by atmospheric gases and/or moisture for extended storage shelf life. The modified reactive sorbents of the present invention can be derived from any suitable form of reactive sorbents capable of absorbing and catalytically reacting or converting a highly toxic material into less toxic products. The modified reactive sorbents of the present invention are simple and relatively cost-efficient to make and implement.

In one aspect of the present invention, there is provided a composition for decontaminating a highly toxic material, which comprises a modified reactive sorbent comprising a reactive sorbent saturated with a sufficient amount of an organic solvent within the pores of the reactive sorbent to yield a non-slurry, free flowing mixture.

In another aspect of the present invention, there is provided a method for making a composition for decontaminating a highly toxic material, which comprises impregnating a reactive sorbent with a sufficient amount of an organic solvent to saturate the pores of the reactive sorbent to yield a non-slurry, free flowing mixture.

In a further aspect of the present invention, there is provided a method for decontaminating a highly toxic material, which comprises applying a modified reactive sorbent comprising a reactive sorbent saturated with a sufficient amount of an organic solvent within the pores of the reactive sorbent to yield a non-slurry, free flowing mixture, to the highly toxic material for a sufficient time and under conditions which are sufficient to produce a reaction product having less toxicity than the highly toxic material.

DETAILED DESCRIPTION OF THE INVENTION

The present invention is directed to a novel composition suitable for use as reactive sorbents and methods for preparing and using these novel reactive sorbents in the form of modified reactive sorbents to decontaminate a wide range of highly toxic materials including chemical warfare agents and/or industrial chemicals, insecticides and the like. In particular, the novel composition of the present invention is formulated to enhance the decontamination performance and capability of existing reactive sorbents. The modified reactive sorbents of the present invention further exhibits enhanced resistance to deactivation of its surface reactivity by atmospheric gases and/or moisture for extended storage shelf life.

In order to solve these and other problems in the art, the present invention provides specifically a modified reactive sorbent exhibiting improved reactivity with a highly toxic material for enhancing decontamination of such highly toxic materials in a rapid and efficient manner. The modified reactive sorbents of the present invention can be derived from any suitable form of reactive sorbents capable of absorbing and catalytically reacting or converting a highly toxic material into less toxic products. The modified reactive sorbents of the present invention are simple and relatively cost-efficient to make and implement.

The modified reactive sorbents of the present invention have been specially treated to enhance diffusion of the highly toxic materials therein, and prevent "pooling" within the pores of the reactive sorbents, while maintaining the modified reactive sorbents in a "dry" free-flowing state for improved handling, application, implementation and subsequent removal. In this manner, the present invention operates to extend the decontamination capability and reliability of existing reactive sorbents.

In one embodiment of the present invention, there is provided a composition for decontaminating a highly toxic material, which comprises a modified reactive sorbent comprising a reactive sorbent saturated with a sufficient amount of an organic solvent within the pores of the reactive sorbent to yield a non-slurry, free flowing mixture.

Accordingly, the invention provides novel compositions for removing and deactivating a wide range of highly toxic materials, including chemical warfare agents. In order to appreciate the scope of the invention, the terms "toxin," "toxic agent," and "toxic material," are intended to be equivalent, unless expressly stated to the contrary. In addition, the terms, "nerve gas," "nerve agent," "neurotoxic," and the like are intended to be equivalent, and to refer to a toxin that acts or manifests toxicity, at least in part, by disabling a component of an animal nervous system, e.g., ACHE inhibitors.

In addition, the use of a term in the singular is intended to encompass its plural in the appropriate context, unless otherwise stated. In addition, reference herein to a toxic agent is intended to encompass chemical warfare agents, including, e.g., toxic organophosphorus-type agents, mustard gas and derivatives, and similar such art-known toxins. In addition, unless otherwise stated, the term toxic agent as used herein is also intended to include toxic industrial chemicals, including, but not limited to, organophosphorus-type insecticides, and the like.

Broadly, the novel compositions provided by the invention are modified reactive sorbents effective for removing, and then deactivating, toxic agents. The term "reactive sorbents" according to the invention includes any composition that is capable of absorbing, or taking up harmful toxic materials including toxic agents, and then catalytically reacting, converting, deactivating or detoxifying at least a portion of the absorbed toxic agent. Thus, the combination of the sorbent and toxic agent is rendered relatively safer to handle after a period of time, relative to the combination of the same amount of toxin under the same conditions with an otherwise equivalent sorbent lacking reactive properties.

For example, the reactive sorbents of the invention can be selected from porous resins, metal oxides, zeolites, aluminum oxides including activated aluminum oxides, magnesium monoperoxyphthalate, metal-exchanged zeolites including silver-exchanged zeolites, transitional metal-exchanged zeolites including sodium zeolite, sorbents impregnated with silver fluoride, dehydroxylated aluminum oxides, optionally combined with reactive catalysts, and the like. The novel reactive sorbent compositions provided by the invention can also optionally be used in combination, either sequentially, and/or as a combined mixture.

Further details on exemplary examples of reactive sorbents suitable for use in the present invention can be found in U.S. Pat. Nos. 6,537,382 and 5,689,038, each being incorporated herein by reference to the extent that their respective contents do not conflict with the disclosure herein.

The modified reactive sorbents of the present invention comprises reactive sorbents having pores that are fully and uniformly filled or saturated with a sufficient amount of an organic solvent, while maintaining the modified reactive sorbents in a dry, free-flowing powder form. The organic solvent occupying the pores of the reactive sorbents can be in a liquid or solid phase. In this manner, the highly toxic material that is taken up by the modified reactive sorbent is solubilized by the organic solvent, thereby facilitating relatively rapid diffusion through the solvent-laced pore network of the modified reactive sorbent, and substantially minimizing "pooling" within the pores. As a result, the surface of the reactive sorbent can rapidly decompose the highly toxic material in an efficient and accelerated manner. Furthermore, the organic solvent seals the surface of the reactive sorbent and prevents undesirable reaction of the reactive sorbent with atmospheric gases and/or moisture that could diminish the reactivity of its surface, thereby extending the storage shelf life of the present composition.

In a preferred embodiment of the present invention, the selection of the organic solvent can be made from any organic solvent capable of dissolving all highly toxic materials including chemical warfare agents and remaining non-reactive with the reactive sorbent, while exhibiting sufficiently low volatility to remain on the sorbent during the decontamination phase. In a more preferred embodiment of the present invention, the organic solvent is an alkane having a chemical formula $C_nH_{2n+2}$, wherein n is at least 9, and preferably at least 20, and combinations thereof. In a most preferred embodiment of the present invention, the organic solvent is selected from mineral oil, paraffin wax, and combinations thereof.

Paraffin wax is particularly desirable for use in the present invention. Paraffin wax is a good sealant, wherein lightly coating and filling the pores of the reactive sorbent operate to preserve the reactivity of sorbents that are susceptible to deactivation by atmospheric gases and/or moisture. Paraffin wax can resist high temperatures, thus substantially minimizing undesirable leeching or bleeding from the reactive sorbent. Paraffin wax is also used in coatings on brushes of dusting/cleaning equipment for water-free removal of dust and dirt from surfaces. Paraffin wax coated reactive sorbents can be easily incorporated for use with such cleaning equipment to provide non-aqueous decontamination of surfaces.

The reactive sorbents preferably exhibit an average particle size of from about 5 to 500 micrometers, and more preferably from about 25 to 200 micrometers. If not commercially available in these ranges, the reactive sorbents can be readily rendered into these ranges by pulverization, milling, and the like. The reactive sorbent further exhibits a surface area in the range of from about 20 to 1500 $m^2/g$, and more preferably from about 500 to 1000 $m^2/g$. The reactive sorbent exhibits a pore volume in the range of from about 0.1 to 1.0 $cm^3/g$, and more preferably from about 0.4 to 0.7 $cm^3/g$.

The amount of organic solvent present to sufficiently saturate the pores of the reactive sorbent, while maintaining the reactive sorbent in a dry, free-flowing powder form, ranges from about 5.0% to 50.0% by weight, preferably 15.0% to 35% by weight, and more preferably 20.0% to 30.0% by weight based on the total weight of the modified reactive sorbent. Alternatively, the amount of the organic solvent is present in a reactive sorbent to solvent weight proportion of about 10 parts reactive sorbent to a range of from about 1 to 5 parts solvent, and more preferably of from about 2 to 3 parts solvent.

In another embodiment of the present invention, there is provided a method for making a composition for decontaminating a highly toxic material, which comprises impregnating a reactive sorbent with a sufficient amount of an organic solvent to saturate the pores of the reactive sorbent to yield a non-slurry, free flowing mixture.

Broadly, and simply by way of example, the modified reactive sorbent is prepared, by placing a reactive sorbent in a mixing vessel for impregnation with the organic solvent. Preferably the reactive sorbent is suitably dried to remove any moisture from the surface and the pores to less than 0.5% water. The reactive sorbent may be suitably dried by simple heating in air, inert atmosphere or under vacuum, for example. Depending on scale, the mixing vessel can be selected from a rotary evaporator, cone blender, ribbon mixer, "V" blender, and the like, or any device or technique suitable for contacting liquids and solids. While the actual amounts can vary in proportion to the desired scale of manufacture. Thus, each 100 g of reactive sorbent is mixed with from about 80 to about 120 g of organic solvent, depending on the porosity of the employed reactive sorbent. For organic solvents that are solid at room temperature (e.g., paraffin wax), the organic solvent must be melted down to liquid phase for impregnating the reactive sorbent. Once in the vessel, the organic solvent in liquid phase is contacted with the reactive sorbent under an inert atmosphere (e.g., dry $N_2$) until insipient wetness is achieved. Alternatively, the reactive sorbent can be contacted with the organic solvent by spraying, dripping and the like.

Once the impregnation step is complete, at least a portion of the excess organic solvent is evaporated. In particular, the excess organic solvent is evaporated from the reactive sorbent such that the resulting reactive sorbent has from about 10% to about 100% of the pore volume filled with the organic solvent, and preferably from about 50 to about 90% of the pore volume filled.

In another embodiment of the present invention, there is provided a method for decontaminating a highly toxic material, which comprises applying a modified reactive sorbent comprising a reactive sorbent saturated with a sufficient amount of an organic solvent to reside in the pores of the reactive sorbent to yield a non-slurry, free flowing mixture, to the highly toxic material for a sufficient time and under conditions which are sufficient to produce a reaction product having less toxicity than the highly toxic material.

The highly toxic materials include chemical warfare agents and/or industrial chemicals, insecticides and the like. In particular the highly toxic materials include, but are not limited to, bis-(2-chloroethyl)sulfide, HD, pinacolyl methylphosphonofluoridate, GD, and O-ethyl S-(2-diisopropylamino)ethyl methylphosphonothioate, VX, neat and thickened forms thereof, and the like.

The highly toxic materials are detoxified and the affected surfaces are decontaminated by contacting the highly toxic materials or surface with a sufficient amount of a modified reactive sorbent of the present invention for a sufficient time and under conditions which are sufficient to produce a reaction product having less toxicity than the chemical warfare agent. It will be understood that the surface decontamination aspect of the invention is achieved by detoxifying the highly toxic material present on the affected surface.

The highly toxic materials are preferably decontaminated by applying the modified reactive sorbent in the form of a powder to the affected (contaminated) areas. The physical contact of the modified reactive sorbent with the highly toxic materials allows the highly toxic materials to be decontaminated and any contaminated surfaces to be rapidly decontaminated by the modified reactive sorbent. While Applicant is not bound by theory, it is believed that a two part decontamination process results from undertaking the methods of the present invention.

During the (first) initial step, the highly toxic materials are adsorbed by the reactive sorbent to eliminate the liquid contact hazard previously associated with the surface. During the second part of the inventive process, the highly toxic materials are decontaminated by hydrolysis or a similar reaction. In the case of VX, the major product of the hydrolysis reaction is ethyl methylphosphonic acid, (based upon the identification of hydrolysis product obtained when the modified reactive sorbents of the present invention are reacted with a VX simulant, O,S-diethyl phenyl phosphonothioate). In the case of HD, the hydrolysis product is thiodiglycol, as determined using the HD simulant 2-chloroethyl phenyl sulfide. GD, on the other hand, would primarily yield pinacolyl methylphosphonic acid based upon the hydrolysis of the GD simulant diisopropyl fluorophosphate.

The methods of the present invention can be carried out by spraying, rubbing, brushing, dipping, dusting, or otherwise contacting the modified reactive sorbents of the invention with a surface or composition that is believed to be in need of such treatment, e.g., because it is, or might be, contaminated with a toxic agent that the modified reactive sorbent will remove and/or deactivate.

In a preferred embodiment of the invention, the modified reactive sorbent is dispersed as a composition that includes the modified reactive sorbent in the form of a dry powder or dust onto contaminated articles or surfaces.

In yet another embodiment of the invention, the reactive sorbent is dispersed in the form of a granulate formed from a powder or dust form of the composition. Such granulated particles, e.g., pellets, can range in size, for example, from sub-millimeter scale beads or grains, up to granules ranging in size from about 1 to about 4 mm, or greater. These optional larger sizes useful for easy distribution of sufficient quantities of the sorbent for decontaminating surfaces containing standing liquids, such as small pools or puddles of water or other solvent, e.g., including spilled fuel and the like. Depending on the nature of the area or equipment to be decontaminated, the granulate is optionally formulated by art-known methods so as to disperse when contacted by the liquid being treated. In a further embodiment, granules that disperse into a powdered form upon contact with a liquid solvent, further include any art-known thickener or gelling agent, to aid in the immobilization of standing liquids suspected of containing toxic contaminants.

In another preferred embodiment, the granulated form is optionally formulated so as to remain cohesive, while absorbing a liquid suspected of containing toxic agents. Advantageously, the used sorbent in granulate form is readily scooped or shoveled off the treated surface, for further processing or disposal.

The artisan will appreciate that selection of the form in which the inventive composition is dispersed will depend upon the physical form of the contaminant(s), the nature of the terrain and/or equipment or personal needing decontamination, and the practical needs of distribution and removal of the used or spent sorbent.

For purposes of the present invention, it will be understood by those of ordinary skill in the art that the term "sufficient" as used in conjunction with the terms "amount", "time" and "conditions" represents a quantitative value that provides a satisfactory and desired result, i.e., detoxifying toxic agents or decontaminating surfaces which have been in contact with toxic agents. The amounts, conditions and time required to achieve the desired result will, of course, vary somewhat based upon the amount of toxic agent present and the area to be treated. For purposes of illustration, the amount of sorbent required for decontaminating a surface is generally, at minimum, an amount which is sufficient to cover the affected area surface. As will be readily understood by those of ordinary skill in the art, the time required to achieve satisfactory detoxification or neutralization will be temperature dependent. For example, at 22° C., most VX, GD, and HD will be detoxified in about 24 hours. Generally, for purposes of the present invention, the range of time required to achieve neutralization will range from about several minutes to about 24 hours or even greater, if necessary. The conditions required for carrying out the claimed methods can generally be described as ambient environmental conditions. For example, the methods can be used at temperatures ranging from about −30° to about 49° C.

The following examples serve to provide further appreciation of the invention but are not meant in any way to restrict the effective scope of the invention.

EXAMPLE 1

Preparation of Alumina

The alumina used was obtained as Selexsorb CDX from Alcoa Inc. of Pittsburgh, Pa., in the form of 7×14 mesh beads. The beads were crushed into a fine powder using a mortar and pestle prior to use.

EXAMPLE 2

Preparation of Decane/Alumina

A volume of decane obtained from Sigma-Aldrich Corp. of St. Louis, Mo., was added to a weighed amount of crushed, "as received" Selexsorb CDX alumina. No drying of the alumina was performed for this sample. The material was then mixed in a sealed vial using a vortex mixer. The decane loading attained was 26.3 wt. %, and the resulting material was still free-flowing and "dry" in appearance.

EXAMPLE 3

Preparation of Decane/Dry Alumina

Crushed Selexsorb CDX alumina was dried in an oven in air at 150° C. A volume of decane was added to a weighed amount of dried Selexsorb CDX alumina and then mixed in a sealed vial using a vortex mixer. The decane loading attained was about 25.9 wt. %, and the resulting material was still free-flowing and "dry" in appearance.

EXAMPLE 4

Preparation of Paraffin Wax/Dry Alumina

A weighed amount of crushed Selexsorb CDX alumina was placed in a glass vial. A weighed amount of paraffin wax obtained from Sigma-Aldrich Corp. of St. Louis, Mo., was added to the top of the alumina in the vial. The vial containing paraffin and alumina was placed into a 105° C. oven (in air), which was above the melting point of the paraffin. The vial was removed from the oven, capped and briefly vortex-mixed. The paraffin loading attained was 25.1 wt. %, and the resulting material was still free-flowing, and "dry" in appearance.

EXAMPLE 5

Demonstration of the Modified Reactive Sorbents as Compared to Control

To demonstrate the present invention, pure liquid decane was selected to confirm the capability of alkanes, preferably higher alkanes, to accelerate the reactions of chemical warfare agents on a reactive sorbent in the form of alumina. The amount of decane added to the alumina was about 26% by weight based on the total weight of the corresponding modified reactive sorbent as this amount was determined to fill the pores of the alumina, while remaining free-flowing and "dry" in appearance. Similarly, 25.1% by weight paraffin was employed. Table 1 below provides the observed half-lives of VX, HD, and GD sorbed on the bare alumina, decane laced alumina and the paraffin laced alumina.

TABLE 1

| Agent | Bare Alumina | Decane/Alumina | Decane/Dry Alumina | Paraffin/Dry Alumina |
|---|---|---|---|---|
| VX | 15.0 days | 3.62 days | 55 minutes | 24.3 minutes |
| HD | 18.2 hours | 1.83 hours | 28.4 minutes | 38.4 minutes |
| GD | 2.7 hours | 6.0 minutes | 16.4 minutes | 5.5 minutes |

For the "as-received" bare alumina, the problem of agent persistency is painfully evident. As shown in the Table, the bare alumina decomposed half the amount of VX in 15 days, HD in 18.2 hours, and GD in 2.7 hours. This trend confirms the notion that sorbed agents primarily diffuse on sorbents via evaporation matching the trend of the agents' volatilities (i.e., GD>HD>>VX).

The addition of decane to the alumina dramatically decreases the observed half-life as liquid-diffusion of the agents is now facilitated by the presence of the decane. As compared to bare alumina, the half-life of VX is reduced from 15.0 days to 3.62 days, HD is reduced from 18.2 hours to 1.83 hours, and GD from 2.7 hours to only 6.0 minutes.

Besides diffusion, the reactivity of the alumina is also influenced by the hydration state of its surface (i.e., how much water is absorbed on the hydroscopic material). As shown by the data in Table 1, further reduction of the agents' half-lives was observed when the alumina was dried prior to loading with decane. The half-life of VX was reduced from 3.62 days to 55 minutes and the half-life of HD was reduced from 1.83 hours to 28.4 minutes. However, the half-life of GD was increased from 6.0 minutes to 16.4 minutes. Each of the agents' half-lives was still significantly shorter than those reacted through the bare alumina.

Test samples of dry alumina loaded with paraffin wax were prepared and tested. The paraffin laced alumina also remained free-flowing and dry in appearance. The data showed similar performance as the decane laced alumina.

In conclusion, a saturating amount of an organic solvent comprising alkanes, preferably higher alkanes, such as liquid decane and solid paraffin wax dramatically enhanced the reaction rates of the chemical warfare agents. The presence of such organic solvents further sealed the surface of the alumina particles from atmospheric gases and moisture which can undesirably deactivate the surface reactivity. This method can generally be applied to any reactive sorbent with similar enhancements in reaction rates and storage shelf life.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A composition for decontaminating a highly toxic material, said composition comprising a modified reactive sorbent comprising a porous reactive sorbent saturated with a sufficient amount of an organic solvent within the pores of the reactive sorbent to yield a non-slurry, free flowing mixture, the organic solvent comprising an alkane having a chemical formula of $C_nH_{2n+2}$, wherein n is at least 9.

2. The composition of claim 1, wherein the organic solvent is in a liquid phase.

3. The composition of claim 1, wherein the organic solvent is in a solid phase.

4. The composition of claim 1, wherein n is at least 20.

5. The composition of claim 1, wherein the alkane is selected from the group consisting of mineral oil, paraffin wax and combinations thereof.

6. The composition of claim 1, wherein the amount of the organic solvent is present in a weight proportion ranging from about 15% to 35% by weight based on the total weight of the composition.

7. The composition of claim 6, wherein the amount of the organic solvent is present in a weight proportion ranging from about 20% to 30% by weight based on the total weight of the composition.

8. The composition of claim 1, wherein the reactive sorbent is selected from the group consisting of zeolite, aluminum oxide, porous resin, and combinations thereof.

9. The composition of claim 1, wherein the reactive sorbent exhibits a surface area in the range of from about 20 to 1500 $m^2/g$.

10. The composition of claim 9, wherein the reactive sorbent exhibits a surface area in the range of from about 500 to 1500 $m^2/g$.

11. The composition of claim 1, wherein the reactive sorbent exhibits a pore volume in the range of from about 0.1 to 1.0 cm³/g.

12. The composition of claim 11, wherein the reactive sorbent exhibits a pore volume in the range of from about 0.4 to 0.7 cm³/g.

13. The composition of claim 1, wherein the amount of the organic solvent is present in a reactive sorbent to solvent weight proportion of about 10 parts reactive sorbent to a range of about 1 to 5 parts solvent.

14. The composition of claim 13, wherein the amount of the organic solvent is present in a reactive sorbent to solvent weight proportion of about 10 parts reactive sorbent to a range of about 2 to 3 parts solvent.

15. The composition of claim 1, wherein the organic solvent is present in an amount sufficient to fill from about 10% to 100% of the pore volume of the reactive sorbent.

16. The composition of claim 15, wherein the organic solvent is present in an amount sufficient to fill from about 50% to 90% of the pore volume of the reactive sorbent.

17. The composition of claim 1, wherein the reactive sorbent is selected from the group consisting of porous resins, metal oxides, zeolites, aluminum oxides, activated aluminum oxides, magnesium monoperoxyphthalate, metal-exchanged zeolites, silver-exchanged zeolites, transitional metal-exchanged zeolites, sodium zeolite, sorbents impregnated with silver fluoride, dehydroxylated aluminum oxides, optionally combined with reactive catalysts, and combinations thereof.

18. The composition of claim 1, wherein the reactive sorbent is a powder having an average particle size ranging from about 5 microns to about 500 microns.

19. The composition of claim 18, wherein the reactive sorbent is a powder having an average particle size ranging from about 25 microns to about 200 microns.

20. A method for making a composition for decontaminating a highly toxic material, comprising impregnating a porous reactive sorbent with a sufficient amount of an organic solvent to saturate the pores of the reactive sorbent to yield a non-slurry, free flowing mixture, the organic solvent comprising an alkane having a chemical formula of $C_nH_{2n+2}$, wherein n is at least 9.

21. The method of claim 20, wherein the organic solvent is present in an amount sufficient to fill from about 10% to 100% of the pore volume of the reactive sorbent.

22. The method of claim 21, wherein the organic solvent is present in an amount sufficient to fill from about 50% to 90% of the pore volume of the reactive sorbent.

23. The method of claim 20, wherein n is at least 20.

24. The method of claim 20, wherein the alkane is selected from the group consisting of mineral oil, paraffin wax and combinations thereof.

25. The method of claim 20, wherein the reactive sorbent is selected from the group consisting of porous resins, metal oxides, zeolites, aluminum oxides, activated aluminum oxides, magnesium monoperoxyphthalate, metal-exchanged zeolites, silver-exchanged zeolites, transitional metal-exchanged zeolites, sodium zeolite, sorbents impregnated with silver fluoride, dehydroxylated aluminum oxides, optionally combined with reactive catalysts, and combinations thereof.

26. The composition of claim 1, wherein the organic solvent is paraffin wax.

27. The composition of claim 1, wherein the reactive sorbent is activated aluminum oxide.

28. The composition of claim 1, wherein the reactive sorbent is activated aluminum oxide and the organic solvent is paraffin wax.

29. The method of claim 20, wherein the organic solvent is paraffin wax.

30. The method of claim 20, wherein the reactive sorbent is activated aluminum oxide.

31. The method of claim 20, wherein the reactive sorbent is activated aluminum oxide and the organic solvent is paraffin wax.

* * * * *